June 15, 1976 R. L. BYRUM Plant Pat. 3,910
ROSE
Filed March 31, 1975
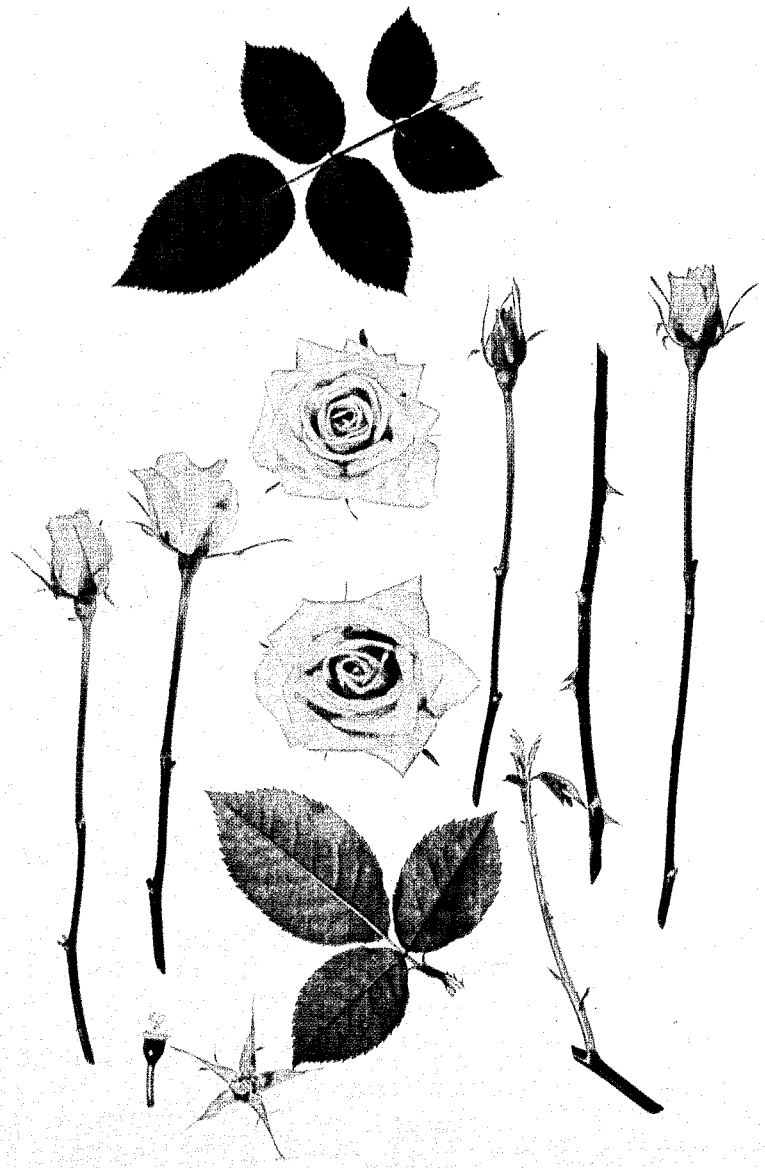

United States Patent

Plant Pat. 3,910

Patented June 15, 1976

3,910

ROSE

Roy L. Byrum, Richmond, Ind., assignor to Joseph H. Hill Company, Richmond, Ind.

Filed Mar. 31, 1975, Ser. No. 563,293

Int. Cl. A01h *5/00*

U.S. Cl. Plt.—26 1 Claim

ABSTRACT OF THE DISCLOSURE

A new variety of rose plant of the floribunda class intended for greenhouse culture for the production of cut flowers, distinguished by its distinctive pink coloring. This new plant is further characterized by a continuous and abundant blooming habit and by its much branched, free, vigorous and upright growth.

BACKGROUND OF THE NEW PLANT

This new rose plant is a result of my crossing of "Junior Bridesmaid" (Plant Pat. No. 2,446), as seed parent, with "Jack Frost" (Plant Pat. No. 2,447) with the object of developing a new pink floribunda variety that would incorporate all of the good qualities of both of its parents. This crossing was made at Richmond, Ind., in the spring of 1969 and the first flowering of this seedling in October of 1970 appeared to indicate that my objectives would be realized. Accordingly asexual propagation of this seedling was done under my direction by budding at Richmond, Ind., and several successive generations of this plant have demonstrated that its novel characteristics hold true from generation to generation and appear to be firmly fixed. Propagation of this new variety of rose plant by budding at Hamilton City, Calif., has also shown the distinctive characteristics of the plant to told true.

DESCRIPTION OF THE DRAWING

This new variety of hybrid rose plant is illustrated by the accompanying photographic drawing which shows, in full color, the form of the fully opened flowers and four stages of the buds, top and under side views of typical leaves, specimens of young and old wood, and side and face views of the reproductive organs as seen when the flower petals have been removed, the colors shown being as nearly true as can be reasonably expected from conventional photographic procedures.

DESCRIPTION OF THE NEW PLANT

The following is a description, in detail, of my new rose plant variety with color designations according to Koster's Color Guide (K) and the Horticultural Colour Chart (W) produced by Robert F. Wilson for the British Colour Council and published by the Royal Horticultural Society at London, England, all of the following comprising data resulting from observations of greenhouse plants grown at Richmond, Ind.

The plant

Origin: Seedling.

Parentage:

*Seed parent.*—Junior Bridesmaid (Plant Pat. No. 2,446).

*Pollen parent.*—Jack Frost (Plant Pat. No. 2,447).

Classification:

*Botanical.*—Rosa hybrid.

*Commercial.*—Floribunda.

Form: Bush.

Habit: Upright and much branched.

Growth: Free and vigorous.

Canes: Of medium diameter, straight and strong.

Main stems:

*Color.*—Spinach Green (W) 0960/2 with streaks of Van Dyck Brown (K) Plate 96.

*Thorns.*—Several, of medium length, downwardly hooked and with a long narrow base. Color: Van Dyck Brown (K) Plate 96.

*Hairs and prickles.*—None.

Branches:

*Color.*—Scheeles Green (W) 860.

*Thorns.*—Several, long, hooked downwardly and each with a long narrow base. Color: Violet Lilac (K) Plate 47 with the color gradually lightening toward the tip.

*Hairs and prickles.*—None.

New shoots:

*Color.*—Lettuce Green (W) 861/2.

*Thorns.*—Several of medium length, hooked downwardly and with a short narrow base. Color: Spinel Red (W) 0023/1.

*Hairs and prickles.*—None.

Foliage:

*Quantity.*—Abundant.

*Leaves.*—Size—medium large. Shape—odd pinnate.

*Leaflets.*—3 or 5 in number. Shape: Ovoid, with round base, acute apex and simply serrate margin. Color: Mature leaf.—upper surface—Spinach Green (W) 0960 (nearest color); under surface—Spinach Green (K) Plate 75 (nearest color); young leaf—upper surface—Veronese Green (W) 660/2 overlaid with shades of Spinel Red (W) 0023/3 through 0023/2, 0023/1 to 0023; under surface—Veronese Green (W) 660/3 overlaid with shades of Spinel Red (W) 0023/2 through 0023/1 to 0023.

*Rachis.*—Medium heavy, with grooved upper side and smooth under side.

*Stipules.*—Very short, very narrow, with short points, and turning out at more than 45° from rachis.

The bud

Before calyx breaks:

*Size.*—Medium small.

*Form.*—Short pointed, with a conspicuous neck and with foliaceous appendages on the bud surface which have slender parts extending beyond the bud tip for a distance of about ¼ of the bud length.

*Color of Calyx.*—Scheeles Green (W) 860/2.

As calyx breaks:

*Color.*—Outside of petal—Rose Madder (W) 23.

As first petal opens:

*Bud size.*—Medium small.

*Form.*—Short pointed.

*Color of petals.*—Outside—Neyron Rose (W) 623 with white base. Inside—Porcelain Rose (W) 620 (nearest color).

Bud opening: Bud opens very well.

Sepals: Permanent, moderately short and straight.

*Color.*—Inside—Scheeles Green (W) 860/2 overlaid with white fuzz; outside—Scheeles Green (W) 860/2.

Peduncle: Erect, strong and of medium diameter and length.

*Bark.*—Smooth. Color: Scheeles Green (W) 860.

*Thorns.*—None.

*Prickles.*—None.

*Hairs.*—Few. Color: Pure White (K) Plate 1.

The flower

Blooming habit: Continuous and abundant.

Size: Medium small, 2 to 3 inches in diameter when fully opened.

Borne: One to several, on strong stems of medium length, commercially disbudded to one flower.

Shape: Full and high centered at first, with petals very tightly rolled outwardly becoming more open as blossom matures with the petals loosely rolled outward.

Petalage: Double—30 to 35 petals regularly arranged.

*Shape of petals.*—Ovate, with mucronate apex.

*Aspect.*—Inside—satiny; outside—shiny.

*Textures.*—Moderately thick and leathery.

*Color of petals*

(A) The following observations were of a newly opened flower in November 1974.

Outside petals

Outside surface—Neyron Rose (W) 623/1 with some white veins and white base.

Inside surface—Dawn Pink (W) 523 with some white at base.

Intermediate petals

Outside surface—Neyron Rose (W) 623/1 with some very light veins and white base.

Inside surface—Dawn Pink (W) 523 with white at base.

Inner petals

Outside surface—Neyron Rose (W) 623/1. Most petals have a white streak in center of petal.

Inside surface—Dawn Pink (W) 523. Some petals have a white streak through petal center. Also, some have one notch at top.

(B) The following are observations of a flower opened for three days.

Outside petals

Outside surface—Neyron Rose (W) 623/1 with some very light veins showing. Also, the petal base is white.

Inside surface—Dawn Pink (W) 523 with white at base.

Intermediate petals

Outside surface—Neyron Rose (W) 623/1. Some petals have a white streak in the center and a white base.

Inside surface—Dawn Pink (W) 523. Some petals have a white streak through the center and some have one notch at the top.

Inner petals

Outside surface—Neyron Rose (W) 623/1. Some petals with a white streak through the center and some petals with one notch at top.

Inside surface—Dawn Pink (W) 523 with white at petal base.

General color effect of open bloom:

*Newly opened flower.*—Dawn Pink (W) 523/2 through 523/1 to 523.

*Three days open flower.*—Dawn Pink (W) 523/2 through 523/1 to 523.

Persistence: Flower petals hang on.

Fragrance: Moderate Tea.

Lasting quality: 5 to 7 days at living room temperatures in November.

Reproductive organs

Stamens: Many in number, arranged regularly about the pistils.

*Filaments.*—Short in length, most with anthers. Color: Mimosa Yellow (W) 602/3.

*Anthers.*—Small in size and all open at the same time. Color: Yellow Ochre (W) 07/3.

*Pollen.*—Abundant. Color: Cadmium Orange (W) 8/3.

Pistils: Many in number.

*Styles.*—Short and of uneven length; moderately thin and bunched. Color: Tyrian Rose (W) 24/2.

*Stigmas.*—Color—Pure White (K) Plate 1.

Ovularies and hips: None.

Aside from being of a distinctively different flower color than either of its parents, this new variety propagates better than its seed parent "Junior Bridesmaid" (Plant Pat. No. 2,446), produces a more vigorous plant in greenhouse and has slightly larger buds and flowers than the seed parent. The new plant does however, have all of the excellent qualities of its pollen parent "Jack Frost" (Plant Pat. No. 2,447).

The new plant is a vigorous and upright growing plant with abundant foliage and continuous production of flowers borne on strong stems of medium length and the keeping quality of the blooms as cut flowers is excellent.

I claim:

1. A new and distinct variety of rose plant substantially as herein shown and described, characterized by the distinctive pink coloration of its flowers, its much branched, free, vigorous and upright growth habit, and by its continuous and abundant production of flowers borne on strong straight stems and having excellent keeping qualities as cut flowers.

No references cited.

ROBERT E. BAGWILL, Primary Examiner